United States Patent [19]

Drewe et al.

[11] 4,118,218

[45] Oct. 3, 1978

[54] FORMULATION PROCESS

[75] Inventors: Nigel Wyndham Drewe, Maidstone; Peter Robin Hodson; Clive Gilroy Robson, both of Tonbridge, all of England

[73] Assignee: Imperial Chemical Industries Limited, London, England

[21] Appl. No.: 695,414

[22] Filed: Jun. 14, 1976

[51] Int. Cl.² .............................................. A01N 9/22
[52] U.S. Cl. .......................................... 71/92; 71/94; 71/DIG. 1
[58] Field of Search .................... 71/DIG. 1, 92, 94; 427/213

[56] References Cited

U.S. PATENT DOCUMENTS

| | | | |
|---|---|---|---|
| 3,085,905 | 4/1963 | Prevot et al. | 427/213 |
| 3,112,220 | 11/1963 | Heiser, Jr. et al. | 427/213 |
| 3,247,014 | 4/1966 | Goldberger et al. | 427/213 X |
| 3,671,213 | 6/1972 | White | 71/94 |
| 3,705,019 | 12/1972 | Mesiah et al. | 71/DIG. 1 |
| 3,920,442 | 11/1975 | Albert et al. | 71/92 |
| 3,967,039 | 6/1976 | Ninane et al. | 427/213 X |

FOREIGN PATENT DOCUMENTS 130,851  12/1965  New Zealand.

*Primary Examiner*—Joseph Paul Brust
*Attorney, Agent, or Firm*—Cushman, Darby & Cushman

[57] ABSTRACT

A process of preparing a solid herbicidal formulation containing a high concentration of a bipyridylium diquaternary salt, which comprises injecting a solution of the bipyridylium salt into a heated fluid bed of a particulate carrier, so that the bipyridylium salt is deposited onto the carrier.

8 Claims, 1 Drawing Figure

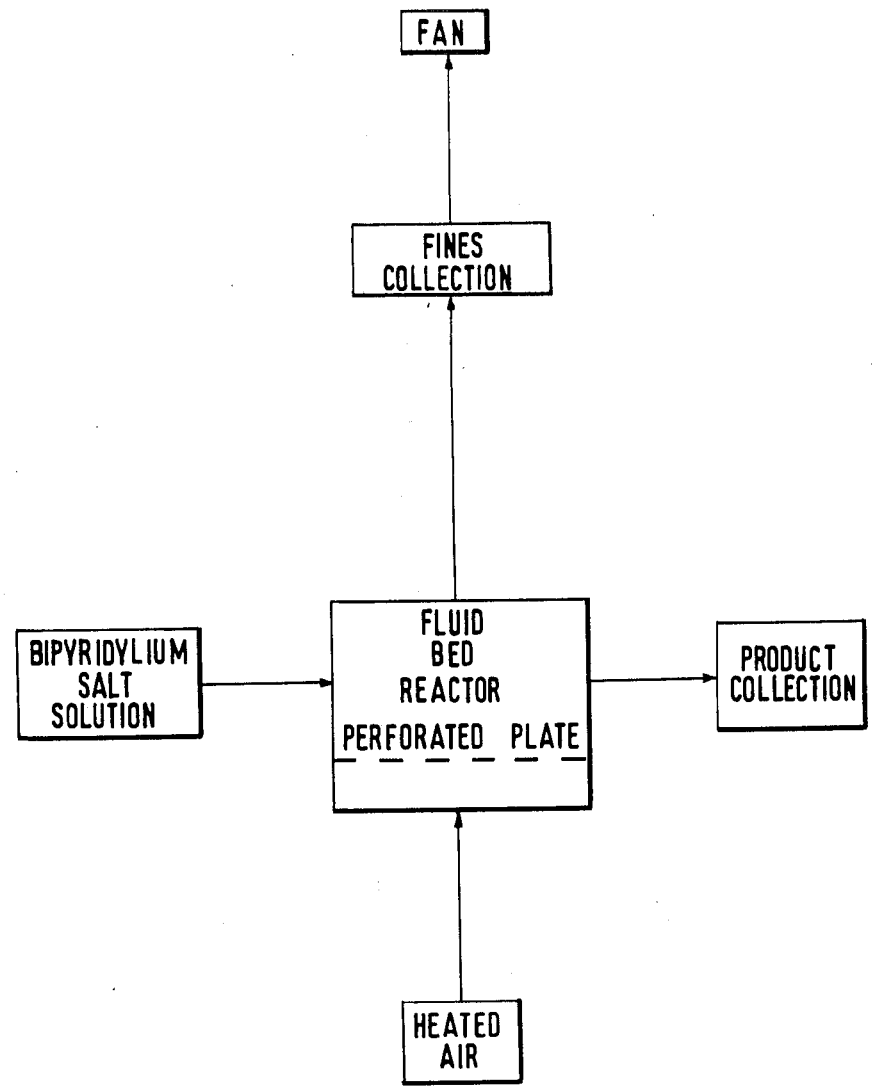

FORMULATION PROCESS

This invention relates to methods of preparing solid formulations of herbicides, particularly bipyridylium herbicides.

Various herbicidal bipyridylium quaternary salts are described in United Kingdom Pat. Specifications Nos. 785,732, 813,531 and 813,532. In general, these compounds are manufactured for use in agriculture in the form of concentrated aqueous solutions. When required for use, these concentrated solutions are diluted with water to form a solution which is then sprayed upon unwanted plants. For various reasons, for example convenience in packaging, it would be convenient for bipyridylium herbicides to be provided in solid form, rather than as aqueous solutions. Various methods have been proposed for the preparation of solid formulations of herbicidal bipyridylium quaternary salts, but so far none of these formulations has proved suitable for wide spread commercial use in agriculture. United Kingdom Pat. Specification No. 813,532 for example discloses dust formulations comprising a mixture of a herbicidal bipyridylium quaternary salt with an inert pulverulent diluent, for example, talc, china clay, gypsum, or basic slag. Such formulations are not convenient for applying bipyridylium herbicides in agriculture and have not gained acceptance in commercial use.

United Kingdom Pat. Specification No. 1,086,937 discloses a process for the preparation of solid herbicidal compositions in which an aqueous solution of a herbicidal bipyridylium quaternary salt is mixed with a hydrate-forming salt in such proportions that the hydrate-forming salt combines with sufficient of the water present to give a solid composition. The compositions prepared in this way have found acceptance in the retail market for use in domestic gardens. However, they are not suitable for large scale agricultural use. Thus, the proportion of active ingredient is relatively low, and the product does not dissolve sufficiently rapidly. Yet another procedure for preparing solid herbicidal compositions is disclosed in Japanese Pat. Publication No. 3381/73. According to this procedure, an aqueous solution of a bipyridylium herbicide is absorbed into preformed granules of a water soluble salt. As in the case of the process of UK Specification No. 1,086,937, only formulations of relatively low concentration of active ingredient can conveniently be made.

A method has now been devised which is capable of preparing a solid granular formulation containing a relatively high proportion of the bipyridylium quaternary salt used as the active ingredient.

According to the present invention, there is provided a process of preparing a solid granular herbicidal composition containing a herbicidal bipyridylium diquaternary salt in association with a solid diluent, which comprises introducing an aqueous solution of a herbicidal bipyridylium diquaternary salt into a fluid bed of particles of a solid diluent maintained at an elevated temperature, whereby the solution of the bipyridylium salt rapidly evaporates and the bipyridylium salt is deposited on the particles of the solid diluent and collecting the solid granular herbicidal composition so prepared. The term fluid bed is well known in the chemical process art; it relates to processes in which a gas is passed through a layer of solid particulate material at such a velocity that the particles become dynamically suspended in the gas stream. The layer (i.e. "bed") of material assumes a highly turbulent condition resembling a boiling liquid. In the present invention it is preferred to use air as the gas for fluidising the solid particulate material. However, other gases (e.g., nitrogen) may be used if desired. The fluid bed is maintained at an elevated temperature by heating the gas stream which fluidises the bed.

The temperature of the heated gas stream is preferably in the range from 100° to 250° C, for example from 120° to 150° C. The fluid bed temperature may range for example from 50° to 100° C. The aqueous solution of the bipyridylium quaternary salt may be introduced into the fluid bed by spraying through one or more spray nozzles. The aqueous solution may itself be heated if desired, but no particular advantage is gained thereby. The concentration of the bipyridylium quanternary salt solution is preferably high, for example at least 200 grams per liter of bipyridylium quaternary cation, so as to reduce the amount of water which has to be evaporated.

Surprisingly, it is not necessary for the solid particulate diluent to be insoluble in water. The evaporation of water from the aqueous solution proceeds so rapidly that even where a water-soluble diluent, for example sodium chloride, is used, no difficulties are encountered with the granules dissolving in the aqueous solution of bipyridylium quaternary salt. Thus both water-soluble and water-insoluble diluents may be used. It is preferred, however, to use diluents which are freely water-soluble, so that when the solid composition of the invention is to be used to kill unwanted plants it may be completely and rapidly dissolved in water to form a spray solution. When an inorganic salt is used as the diluent, it is preferred that the salt should be substantially free of water of crystallization, since hydrated salts may decrepitate when placed in the heated air stream. Salts which react as alkalis in aqueous solution, for example salts which have a pH of more than about 8 when dissolved in water (for example sodium carbonate) are preferably not used as solid diluents in the invention, because of the deleterious effects they may have on the active ingredients of the composition, bipyridylium quaternary salts being less stable in solutions of high pH.

The velocity of the air stream required to fluidise the solid particulate diluent will depend upon a number of factors, for example upon the particle size of the diluent and upon its density. A suitable velocity is readily established by operation of the process, the technology of fluid bed processes being well known to those skilled in the art, but by way of example, a linear air velocity of 0.9 to 1.1 meters per second has been found suitable to maintain a bed of sodium chloride in a fluid condition.

Herbicidal bipyridylium quaternary salts which may be used as the active ingredients of the compositions of the invention include those of the following formulae:

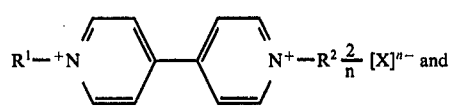 and

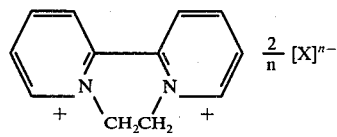

wherein $R^1$ and $R^2$, which may be the same or different, each stand for an alkyl or alkenyl radical of 1 to 4 carbon atoms, which may be substituted by a hydroxy, carboxy, alkoxy, alkylcarbonyl, alkoxycarbonyl, carbamoyl, or N-alkyl-substituted carbamoyl radical, or a halogen atom; $X^{n-}$ represents an anion and n is 1, 2, 3 or 4. Preferred alkoxy groups are those containing 1 to 4 carbon atoms. Preferred alkylcarbonyl and alkoxycarbonyl groups are those containing from 2 to 5 carbon atoms. Preferred N-alkyl substituted carbamoyl radicals are those in which the N-alkyl substituent or substituents contain from 1 to 4 carbon atoms.

Examples of herbicidal bipyridylium diquaternary salts include those listed below:
  1,1′-ethylene-2,2′-bipyridylium dibromide (diquat dibromide)
  1,1′-dimethyl-4,4′-bipyridylium dichloride (paraquat dichloride)
  1,1′-di-2-hydroxyethyl-4,4′-bipyridylium dichloride
  1,1′-bis-3,5-dimethylmorpholinocarbonylmethyl-4,4′-bipyridylium dichloride (morfamquat dichloride)
  1-(2-hydroxyethyl)-1′-methyl-4,4′-bipyridylium dichloride
  1,1′-di-carbamoylmethyl-4,4′-bipyridylium dichloride
  1,1′-bis-N,N-dimethylcarbamoylmethyl-4,4′-bipyridylium dichloride
  1,1′-bis-N,N-diethylcarbamoylmethyl-4,4′-bipyridylium dichloride
  1,1-di-(piperidinocarbonylmethyl)-4,4′-bipyridylium dichloride
  1,1′-diacetonyl-4,4′-bipyridylium dichloride
  1,1′-diethoxycarbonylmethyl-4,4′-bipyridylium dibromide
  1,1′-diallyl-4′-bipyridylium dibromide The names in brackets alongside some of the compounds in the above list are the accepted common names for the cationic portion of the compounds. Thus 'paraquat' is the common name for the 1,1′-dimethyl-4,4′-bipyridylium cation. Paraquat is a particularly preferred bipyridylium compound for use in the compositions of the invention.

Since the herbicidal effect of a bipyridylium quaternary cation is independent of the nature of the associated anion, the choice of the anion is a matter of convenience, depending, for example, on cost. Preferably the anion is one which gives rise to a salt of convenient water solubility. Examples of anions, which may be mono- or poly-valent, include acetate, benzenesulphonate, benzoate, bromide, butyrate, chloride, citrate, fluorosilicate, fumarate, fluoroborate, iodide, lactate, malate, maleate, methylsulphate, nitrate, propionate, phosphate, salicylate, succinate, sulphate, thiocyanate, tartrate, and p-toluenesulphonate. The salt of the herbicidal bipyridylium cation may be formed from a number of similar anions or mixtures of different ones. A salt having any particular desired anion may be prepared either by direct synthesis from reactants which include the desired anion, or by exchanging the anion of a previously prepared salt for the preferred anion by methods well known in the art, for example by passage of a solution of the previously prepared salt through an ion-exchange resin. For reasons of convenience and economy, the chloride anion is a particularly preferred anion.

Since the characteristic herbicidal activity of a salt of a herbicidal bipyridylium quaternary cation resides in the cation only, it is customary to quote concentrations of active ingredient and rates of application in terms of the amount of bipyridylium quaternary cation used, thus avoiding the inconvenience of having to quote different application rates for different salts of the same bipyridylium quaternary cation. Application rates and concentrations quoted in this specification therefore relate to the amount of bipyridylium quaternary cation unless otherwise stated.

As noted above, in operating the process of the invention, it is preferred to use an aqueous solution containing a high concentration of bipyridylium quaternary cation, for example at least 200 grams per liters. Concentrations as high as 360 grams per liter may conveniently be employed. The product of the process may also contain a relatively high proportion of the bipyridylium cation used as the active ingredient; for example, concentrations of 20% by weight of bipyridylium cation are readily achieved and higher concentrations for example up to 28% by weight or more can be conveniently prepared. Preferably the product contains at least 10% by weight of bipyridylium cation.

The process of the invention may be operated either batchwise or as a continuous process.

The time taken to complete the preparation of the product will be dependent for example upon the temperature and velocity of the heated air stream. By way of example, in a typical batch preparation, 5 kilograms of sodium chloride were fluidised in an airstream having a velocity of 60 meters per minute and a temperature of 130° C on the inlet side of the fluidised bed. A solution of paraquat dichloride (6 liters; 360 grams paraquat per liter) was injected into the fluidised bed through a spray nozzle over a period of 1 hour. The product collected at the end of this time was a non-dusty, free-flowing granular solid containing 27% by weight of paraquat, and was moisture-free. The average particle size of the granules was in the range 1 to 2 millimeters and the bulk density was 0.88 grams per milliliter.

If desired, further ingredients may be incorporated in the composition of the invention, for example surface-active agents. This may be done in various ways; for example a surface-active agent may be incorporated into the aqueous solution of bipyridylium salt which is introduced into the fluid bed. Alternatively the bipyridylium solution and the solution of the surface-active agent may be introduced separately from one another into the fluidised bed. The amount of surface-active agent used may be, for example, from 10 to 20% by weight of the amount of bipyridylium cation in the composition, although larger or smaller amounts may be appropriate depending upon the application intended for the product.

Preferably, the surface-active agent used is a cationic or non-ionic surface-active agent. The choice of a particular surface-active agent is within the competence of one skilled in the art of pesticide formulation. By way of example, however, non-ionic surface active agents useful in the compositions of the invention include the condensation products of ethylene oxide with fatty alcohols such as oleyl alcohol and cetyl alcohol, or with alkyl phenols such as octylphenol, nonylphenol and octylcresol. Other non-ionic agents are the partial esters derived from long chain fatty acids and hexitol ahydrides, for example sorbitan monolaurate; the condensation products of the said partial esters with ethylene oxide; and the lecithins. Examples of cationic surface active agents include quaternary salts and condensates of ethylene oxide with amines, for example the substances sold under the Trade Mark "Ethomeen" "Ethoduomeen" "Duoquad" and "Arquad."

The process of the invention may be carried out in conventional fluid bed reactor apparatus. Fluid bed technology is well known to those skilled in the chemical process art. The reactor itself comprises a generally tubular or cylindrical vessel mounted with its long axis vertical, and having a perforated plate closing its lower end. The solid particulate material to be fluidised is filled into the reactor and lies on the perforated plate. The gas which is used to fluidise the material is forced through the perforated plate under pressure and passes upwards through the material. It is preferred to maintain the pressure on the downstream side of the perforated plate at slightly below the atmospheric pressure outside the apparatus, for example by means of a fan arranged to exhaust the effluent air from the reactor. In this way, escape of fine particles from the apparatus is prevented should a leak develop in the walls thereof. In the process of the present invention it is preferred to pass the effluent air from the reactor through apparatus (for example, a cyclone) to collect fine dusty particles which are too small to remain in the fluid bed and which are swept through the reactor by the air-stream. As mentioned above the aqueous solution of the bipyridylium salt may be introduced into the fluid bed by spraying through one or more spray nozzles. These may be mounted, for example, in the wall of the fluid bed reactor or in the centre of the perforated plate. Conveniently the solution may be pumped through a metering pump to enable measurement of the quantity introduced to be regulated.

The apparatus is shown schematically in a block diagram in the accompanying drawing.

The following Example illustrates the invention.

EXAMPLE

The process of the invention was operated using granular calcium chloride and sodium chloride as solid particulate diluents. The bipyridylium salt used was paraquat dichloride, at a concentration of 360 grams of paraquat per liter. In the run with sodium chloride, a surface-active agent comprising a condensate of from 7 to 8 molar proportions of ethylene oxide with p-nonylphenol and sold under the Trade Mark "Lissapol" NX was mixed with the paraquat dichloride solution in the proportion of 4 parts paraquat to 1 part of "Lissapol" NX, and sprayed as a homogeneous mixture. The products from the two runs were uniform, free-flowing, non-dusty granules having an average particle size in the range from 1 to 2 millimeters. The operating conditions are summarised in Table I.

TABLE I

| Run No | Solid Diluent | Time (min.) | Bed Inlet Temperature °C | Average Bed Temperature | Air Velocity cu. metres per sec. |
|---|---|---|---|---|---|
| 1 | Calcium chloride | 85 | 130 | 93 | 1.1 |
| 2 | Sodium chloride | 70 | 130 | 86 | 1.0 |

The analysis and yield of products are given in Table II.

TABLE II

| Run No | Diluent Charged (kg) | Paraquat (kg) | Lissapol NX (kg) | Paraquat Content Of Product % w/w | Lissapol Content Of Product (Calculated) % w/w | Bulk Density | Moisture Content Of Product (Analysis) | Yield (kg) |
|---|---|---|---|---|---|---|---|---|
| 1 | 4.54 | 2.06 | — | 27.8 | — | 0.80 | Trace | 7.30 |
| 2 | 3.60 | 1.90 | 0.475 | 28.3 | 7:0 | 0.80 | Trace | 6.70 |

We claim:

1. A process of preparing a solid granular herbicidal composition containing a herbicidal bipyridylium diquaternary salt in association with an inert, water-soluble, solid diluent therefor, which comprises introducing an aqueous solution of a herbicidal bipyridylium diquaternary salt into a gaseous fluidised bed of particles of the solid, water-soluble, diluent maintained at an elevated temperature such that the solution of the bipyridylium salt rapidly evaporates to deposit the bipyridylium salt as a coating on the particles of the solid diluent without dissolving the diluent particles, and collecting the solid granular herbicidal composition so prepared, the concentration of herbicidal bipyridylium diquaternary salt in the aqueous solution introduced into the fluidised bed being at least 200 grams per liter, and the collected composition containing at least 10% by weight of bipyridylium cation.

2. A process as claimed in claim 1 wherein the solid diluent is water-soluble and the fluid bed is maintained at a temperature of from 50° to 100° C.

3. A process as claimed in claim 1 wherein the gas used to fluidise the particles of solid diluent is air.

4. A process as claimed in claim 1 wherein the herbicidal bipyridylium diquaternary salt comprises a compound of the formula:

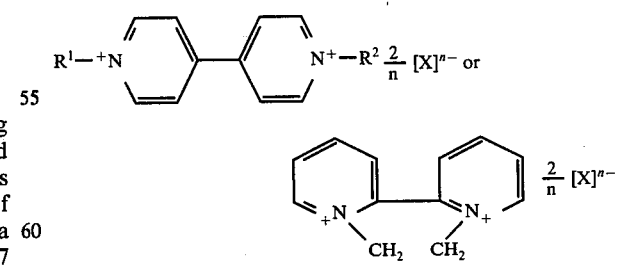

wherein $R^1$ and $R^2$, which may be the same or different, each stand for an alkyl or alkenyl radical of up to 4 carbon atoms, optionally substituted by a hydroxy, carboxy, alkoxy, alkylcarbonyl, alkoxycarbonyl, carbamoyl, or N-substituted carbamoyl radical, or a halogen atom; X represents an anion and n is 1, 2, 3, or 4.

5. A process as claimed in claim 1 wherein the herbicidal bipyridylium diquaternary salt is paraquat dichloride and the composition is collected in the form of a nondusty, free-flowing granular solid.

6. A process as claimed in claim 1 which further comprises introducing a solution of a surface-active agent into the fluidised bed whereby the solution rapidly evaporates to deposit the surface-active agent on to the particles of the solid diluent.

7. A process as claimed in claim 1 wherein the solid diluent is an inorganic salt.

8. A process as claimed in claim 7 wherein the solid diluent is sodium chloride or calcium chloride.

* * * * *

UNITED STATES PATENT OFFICE
CERTIFICATE OF CORRECTION

Patent No. 4,118,218  Dated October 3, 1978

Inventor(s) Nigel Wyndham DREWE; Peter Robin HODSON; and Clive Gilroy ROBSON

It is certified that error appears in the above-identified patent and that said Letters Patent are hereby corrected as shown below:

In the heading of the patent, add:

--[30]  Foreign Application Priority Data

June 16, 1975  Great Britain.... 25537/75--

Signed and Sealed this

Thirteenth Day of February 1979

[SEAL]

Attest:

RUTH C. MASON
Attesting Officer

DONALD W. BANNER
Commissioner of Patents and Trademarks